United States Patent
Cuesta et al.

(10) Patent No.: US 7,585,333 B2
(45) Date of Patent: Sep. 8, 2009

(54) TRIAZINYLAMINOSTILBENE DISULPHONIC ACID MIXTURES

(75) Inventors: Fabienne Cuesta, Waldighoffen (FR); Ted Deisenroth, Brookfield, CT (US); Peter Rohringer, Schönenbuch (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 437 days.

(21) Appl. No.: 10/585,956

(22) PCT Filed: Jan. 10, 2005

(86) PCT No.: PCT/EP2005/050070

§ 371 (c)(1), (2), (4) Date: Jul. 13, 2006

(87) PCT Pub. No.: WO2005/068597

PCT Pub. Date: Jul. 28, 2005

(65) Prior Publication Data

US 2008/0307585 A1    Dec. 18, 2008

(30) Foreign Application Priority Data

Jan. 20, 2004   (EP)  ................... 04100158

(51) Int. Cl.
*D06L 3/12*   (2006.01)
*C07D 251/00*  (2006.01)

(52) U.S. Cl. ............ 8/648; 8/638; 8/650; 8/115.6; 8/183; 8/189; 8/190; 544/180

(58) Field of Classification Search .............. 8/495, 8/638, 648, 650, 115.6, 183, 189, 190; 544/180
See application file for complete search history.

(56) References Cited

U.S. PATENT DOCUMENTS

| | | | | |
|---|---|---|---|---|
| 6,015,504 | A | 1/2000 | Reinehr et al. | 252/8.91 |
| 6,302,999 | B1 * | 10/2001 | Engelhardt et al. | 162/135 |
| 2002/0084049 | A1 | 7/2002 | Engelhardt et al. | 162/158 |

FOREIGN PATENT DOCUMENTS

| | | |
|---|---|---|
| DE | 10150894 | 4/2003 |
| WO | 03/070869 | 8/2003 |

OTHER PUBLICATIONS

STIC Search Report dated Nov. 25, 2008.*

* cited by examiner

*Primary Examiner*—Eisa B Elhilo
(74) *Attorney, Agent, or Firm*—Joseph C. Suhadolnik

(57) ABSTRACT

The present invention relates to a fluorescent whitening agent comprising a mixture of two symmetrically and one asymmetrically substituted triazinylaminostilbene disulphonic acids, certain novel derivatives, a process for their preparations and use of the mixture for whitening synthetic or natural organic materials, especially paper and for the fluorescent whitening and improvement of sun protection factors of textile materials.

16 Claims, No Drawings

TRIAZINYLAMINOSTILBENE DISULPHONIC ACID MIXTURES

The present invention relates to a fluorescent whitening agent comprising a mixture of two symmetrically and one asymmetrically substituted triazinylaminostilbene disulphonic acids, novel asymmetrically substituted derivatives, a process for their preparations and use of the mixture for whitening synthetic or natural organic materials, especially paper and for the fluorescent whitening and improvement of sun protection factors of textile materials.

Mixtures of triazinylaminostilbene sulphonic acids for whitening paper have been disclosed in U.S. Pat. No. 3,132,106. However such mixtures are restricted to the tetrasulphonic acids, which are especially suitable for whitening paper in pulp applications and less desirable for present day whitening techniques such as coating or size-press applications.

Surprisingly, it has now been found that mixtures of triazinylaminostilbene disulphonic acids are eminently suitable for use, not only in pulp applications, but also in paper coating and size-press applications, where they exhibit extremely high degrees of whiteness and, furthermore, may be readily formulated as stable liquid compositions.

Accordingly, the present invention relates to a fluorescent whitening agent, which comprises a mixture of compounds of the formulae

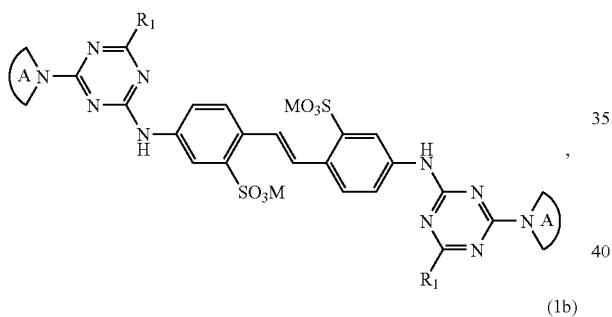

(1a)

,

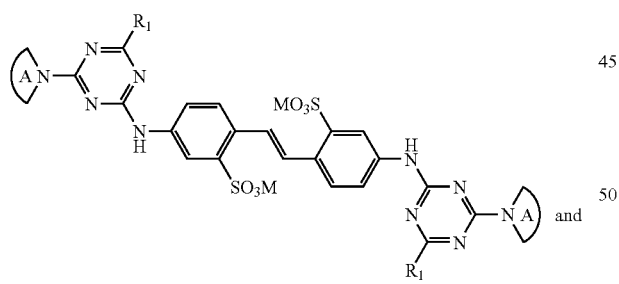

(1b)

and

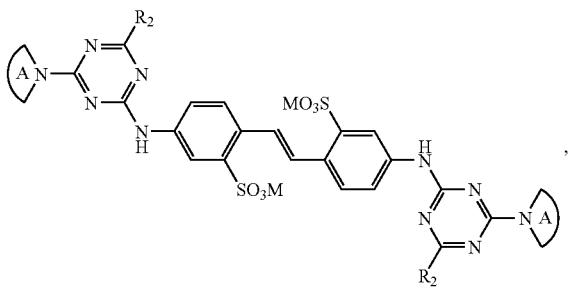

(1c)

in which $R_1$ and $R_2$ are different and each represents —$NH_2$, —$NHC_1$-$C_4$alkyl, —$N(C_1$-$C_4$alkyl$)_2$, —$NHC_2$-$C_4$ hydroxyalkyl, —$N(C_2$-$C_4$hydroxyalkyl$)_2$, —$N(C_1$-$C_4$alkyl)($C_2$-$C_4$ hydroxyalkyl), a morpholino residue or an amino acid or an amino acid amide residue from which a hydrogen atom has been removed from the amino group, each of the rings designated as A represent a 5- or 6-membered saturated heterocycle, which may contain one further heteroatom and M represents hydrogen, an alkali metal atom, ammonium or a cation formed from an amine.

The 5- or 6-membered saturated heterocyclic ring A is preferably a pyrrolidino, piperidino or, especially, a morpholino residue, such that preferred fluorescent whitening agent mixtures comprise the compounds of formulae

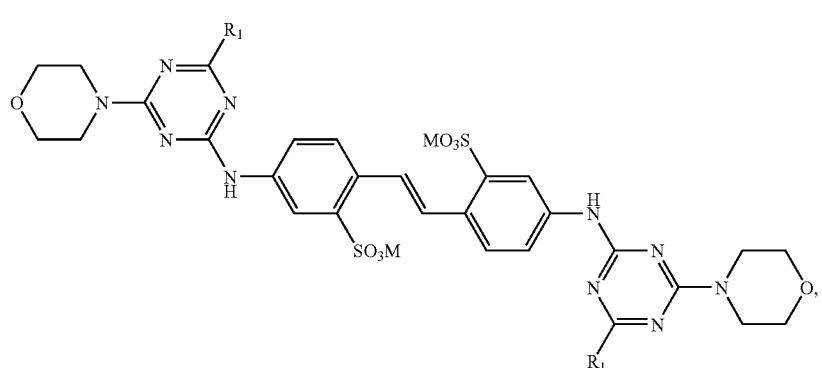

(2a)

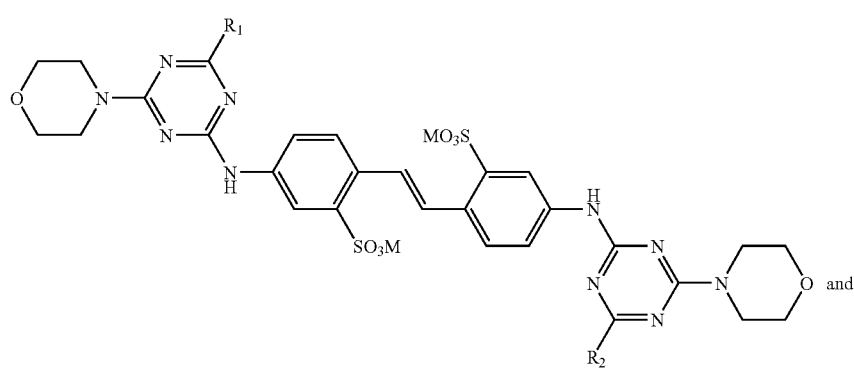

(2b)

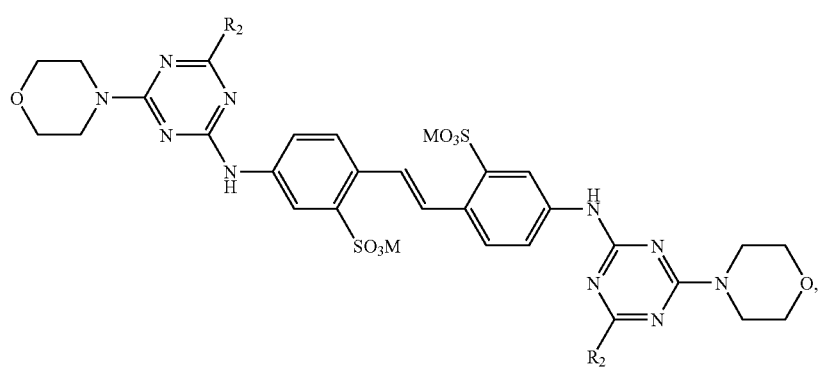

(2c)

in which

R₁, R₂ and M are as defined previously.

When $R_1$ and/or $R_2$ represent an amino acid or amino acid amide residue, this is preferably of the formula

   (3)

or

   (4), in which each $R_3$ and $R_{3'}$, independently, represent hydrogen or a group having the formula

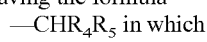 in which $R_4$ and $R_5$, independently, are hydrogen or $C_1$-$C_4$alkyl optionally substituted by one or two substituents selected from the group consisting of hydroxy, thio, methylthio, amino, carboxy, sulfo, phenyl, 4-hydroxyphenyl, 3,5-diiodohydroxyphenyl, β-indolyl, β-imidazolyl and NH=C(NH₂)NH—.

More preferably, the residues $R_1$, and/or $R_2$ are derived from glycine, alanine, sarcosine, serine, cysteine, phenylalanine, tyrosine (4-hydroxyphenylalanine), diiodotyrosine, tryptophan (β-indolylalanine), histidine (β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δdiaminovaleric acid), lysine (α,ε-diaminocaproic acid), aspartic acid (aminosuccinic acid), glutamic acid (α-minoglutaric acid), threonine, hydroxyglutamic acid and taurine, as well as mixtures and optical isomers thereof, or from iminodiacetic acid or from N-(propionamido)-N-(2-hydroxyethyl)amine.

Most preferably, however, $R_1$ and/or $R_2$ represent —N($C_1$-$C_4$alkyl)₂, —NHC₂-$C_4$hydroxyalkyl, —N($C_2$-$C_4$hydroxyalkyl)₂, —N($C_1$-$C_4$allyl)($C_2$-$C_4$hydroxyalkyl), a morpholino residue or a residue derived from glycine, sarcosine, taurine, glutamic acid, aspartic acid, iminodiacetic acid or from N-(propionamido)-N-(2-hydroxyethyl)amine, and, especially, $R_1$ represents a diethylamino, a mono-(2-hydroxyethyl)amino, a di-2-hydroxyethyl)amino, a dl-(2-hydroxypropyl)amino, an N-(2-hydroxyethyl)-N-methylamino, a morpholino, an N-(propionamido)-N-(2-hydroxyethyl)amino or a sarcosine residue and $R_2$ represents an aspartic acid or a glycine residue.

In the compounds of formulae (1a)-(1c), M represents hydrogen, lithium, potassium, sodium, ammonium, mono-, di-, tri- or tetra-$C_1$-$C_4$alkylammonium, mono-, di- or tri-$C_1$-$C_4$hydroxyalkylammonium or ammonium that is di- or tri-substituted with a mixture of $C_1$-$C_4$alkyl and $C_1$-$C_4$hydroxyalkyl groups, i.e. $H_2N^+(C_1$-$C_4$alkyl)($C_1$-$C_4$hydroxyalkyl) and $HN^+(C_1$-$C_4$alkyl)$_m$($C_1$-$C_4$hydroxyalkyl)$_n$, where n and m represent 1 or 2, but preferably M represents hydrogen, potassium or sodium.

In a most preferred aspect, the invention relates to a fluorescent whitening agent comprising a mixture of the compounds of formulae (2a), (2b) and (2c) in which $R_1$ represents mono-(2-hydroxyethyl)amino, di-(2-hydroxyethyl)amino, di-(2-hydroxypropyl)amino, diethylamino or an N-(2-hydroxyethyl)-N-methylamino, $R_2$ represents an aspartic acid or a glycine residue and M represents sodium.

Where $R_1$, $R_2$ and/or $R_3$ contain $C_1$-$C_4$alkyl radicals, these may be branched or unbranched and are, for example, methyl, ethyl, n-propyl, isopropyl or n-butyl; isobutyl or tert-butyl; whilst $C_1$-$C_4$alkoxy is, for example, methoxy, ethoxy, propoxy, isopropoxy, n-butoxy, isobutoxy or tert-butoxy. $C_1$-$C_4$hydroxyalkyl may, for example, be hydroxymethyl, hydroxyethyl, hydroxypropyl or hydroxybutyl.

The compound mixture of formulae (1a), (1b) and (1c) may be prepared by reacting, under known reaction conditions, cyanuric chloride, successively, in any desired sequence, with each of 4,4'-diaminostilbene-2,2'-disulphonic acid, an appropriate heterocylic compound, for example, pyrrolidine, piperidine or, especially, morpholine, an amino compound $R_1H$ and an amino compound $R_2H$, or, alternatively a mixture of amino compounds $R_1H$ and $R_2H$, $R_1$ and $R_2$ being as defined previously. However, preferably, cyanuric chloride is initially reacted with 4,4'-diaminostilbene-2,2'-disulphonic acid, followed by reaction with morpholine and, finally, with a mixture of amino compounds $R_1H$ and $R_2H$.

Depending on the amounts and proportions of the amines $R_1H$ and $R_2H$ and whether they are added sequentially or simultaneously as a mixture, the proportions of the compounds (1a), (1b) and (1c) can be varied considerably. Thus, the present invention relates to a fluorescent whitening agent which comprises a mixture of the compounds (1a), (1b) and (1c) wherein each of the components are present in a molar ratio of between 5 and 80%, preferably they are present in the approximate molar ratios of 5-45% of the compound of formula (1a), 15-60% of the compound of formula (1b) and 5-45% of the compound of formula (1c). More preferably, the compounds (1a), (1b) and (1c) are present in the approximate molar ratios of 20-50% of the compound of formula (1a), 30-60% of the compound of formula (1b) and 10-40% of the compound of formula (1c).

Naturally, such compositions may also be obtained simply by mechanical mixing of the individual components in the desired proportions. In this case it is necessary to obtain the individual components as pure substances. Whilst some of the components of formulae (1a) and (1c) are known compounds, the majority of those symmetrical derivatives in which $R_1$ and $R_2$ represent an amino acid residue from which a hydrogen atom has been removed from the amino group in addition to compounds of formula (1b) are new.

Consequently, one further aspect of the invention is a compound of formula

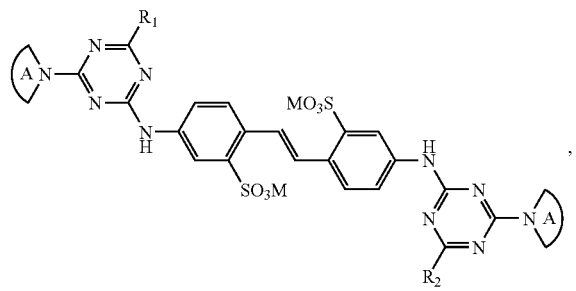

in which $R_1$, $R_2$, A and M, as well as their preferences, are as defined previously, whilst a second further aspect of the invention relates to a compound of formula

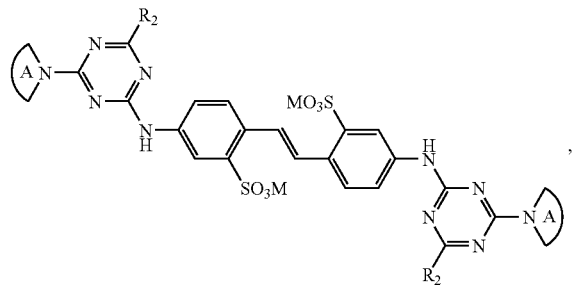

in which $R_2$ is an amino acid or amino acid derivative from which a hydrogen atom has been removed from the amino group, whereby the residue is derived from alanine, sarcosine, serine, cysteine, phenylalanine, tyrosine (4-hydroxyphenylalanine), diiodotyrosine, tryptophan (β-indolylalanine), histidine (β-imidazolylalanine), (α-aminobutyric acid, methionine, valine (a aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine or hydroxyglutamic acid, as well as mixtures and optical isomers thereof, or from iminodiacetic acid or from N-(propionamido)-N-(2-hydroxyethyl)amine or the corresponding propionic acid and the heterocyclic ring A and the symbol M, as well as their preferences, are as previously defined.

The compound of formula (1b) may either be obtained by purification of the mixture obtained as described above, or, for example, by the following reaction sequence:

i) Reaction of cyanuric chloride with 4-amino-4'-nitrostilbene-2,2'-disulphonic acid with cyanuric chloride;

ii) reaction of the dichloro intermediate with the appropriate heterocyclic compound, for example, pyrrolidine, piperidine or, especially, morpholine;

iii) reaction of the monochloro intermediate with an amine $R_1H$ or —$R_2H$;

iv) reduction of the nitrostilbene to the aminostilbene;

v) reaction with cyanuric chloride;

vi) reaction of the dichloro intermediate with the appropriate heterocyclic compound, for example, pyrrolidine, piperidine or, especially, morpholine and vii) reaction of the monochloro intermediate with an amine $R_2H$ or $R_1H$.

Naturally, this reaction sequence may be performed in any desirable and practical order.

A further aspect of the invention is the use of a composition for whitening synthetic or natural organic materials, which contains water, a fluorescent whitening agent which comprises a mixture of the compounds (1a), (1b) and (1c) and, optionally, auxiliaries.

More specifically, such brightener compositions contain water and, in each case based on the weight of the formulation, from 3 to 35% by weight, preferably from 5 to 25 by weight of the above defined fluorescent whitening agent mixture and also 0 to 60%, preferably 5 to 50% by weight, of auxiliaries.

Suitable auxiliaries include, for example, anionic or non-ionic dispersants from the class of ethylene oxide adducts with fatty alcohols, higher fatty acids or alkyl phenols or ethylenediamine ethylene oxide-propylene oxide adducts, copolymers of N-vinylpyrrolidone with 3-vinylpropionic acid, water retention aids, such as ethylene glycol, glycerol or sorbitol, or biocides.

Further auxiliaries useful both for the production of stable liquid formulations and also for enhancing the whitening effect of the mixtures are, for example, polyethylene glycols. Such polyethylene glycols may have average molecular weights varying over a wide range, for example from about 200 to about 2000, the molecular weight range of about 1500 being especially suitable.

Most of the compositions comprising a mixture of the compounds of formulae (1a), (1b) and (1c) are excellent fluorescent whitening agents for substrates such as textiles, for the addition to detergent compositions and, especially for the fluorescent whitening of paper.

When used for the fluorescent whitening of paper, the composition, which contains water, a fluorescent whitening agent which comprises a mixture of the compounds (1a), (1b) and (1c) and, optionally, auxiliaries, may be applied to the paper substrate in the pulp mass, in the form of a paper coating composition, or directly in the size press or metering press.

In one preferred aspect, the present invention provides a method for the fluorescent whitening of a paper surface, comprising contacting the paper surface with a coating composition comprising a white pigment; a binder dispersion;

optionally a water-soluble co-binder; and sufficient of a fluorescent whitening agent comprising a mixture of the compounds of formulae (1a), (1b) and (1c) according to the present invention, to ensure that the treated paper contains 0.01 to 1% by weight, based on the white pigment, of fluorescent whitening agent.

As the white pigment component of the paper coating composition used according to the method of the present invention, there are preferred inorganic pigments, e.g., aluminium or magnesium silicates, such as China clay and kaolin and, further, barium sulfate, satin white, titanium dioxide, calcium carbonate (chalk) or talcum; as well as white organic pigments.

The paper coating compositions used according to the method of the present invention may contain, as binder, inter alia, plastics dispersions based on copolymers of butadiene/styrene, acrylonitrile/butadiene/styrene, acrylic acid esters, acrylic acid esters/styrene/acrylonitrile, ethylene/vinyl chloride and ethylene/vinyl acetate; or homopolymers, such as polyvinyl chloride, polyvinylidene chloride, polyethylene and polyvinyl acetate or polyurethanes. A preferred binder consists of styrene/butyl acrylate or styrene/butadiene/acrylic acid copolymers or styrene/butadiene rubbers. Other polymer lattices are described, for example, in U.S. Pat. Nos. 3,265, 654, 3,657,174, 3,547,899 and 3,240,740.

The optional water-soluble protective colloid may be, e.g., soya protein, casein, carboxymethylcellulose, natural or modified starch, chitosan or a derivative thereof or, especially, polyvinyl alcohol. The preferred polyvinyl alcohol protective colloid component may have a wide range of saponification levels and molecular weights; e.g. a saponification level ranging from 40 to 100; and an average molecular weight ranging from 10,000 to 100,000.

Recipes for coating compositions for paper are described, for example, in J. P. Casey "Pulp and Paper"; Chemistry and Chemical Technology, 2nd edition, Volume III, pages 1684-1649 and in "Pulp and Paper Manufacture", 2nd and 5th edition, Volume II, page 497 (McGraw-Hill).

The paper coating compositions used according to the method of the present invention preferably contain 10 to 70% by weight of a white pigment. The binder is preferably used in an amount, which is sufficient to make the dry content of polymeric compound up to 1 to 30%, by weight, preferably 5 to 25% by weight, of the white pigment. The amount of fluorescent brightener preparation used according to the invention is calculated so that the fluorescent brightener is preferably present in amounts of 0.01 to 1% by weight, more preferably 0.05 to 1% by weight, and especially 0.05 to 0.6% by weight, based on the white pigment.

The paper coating composition used in the method according to the invention can be prepared by mixing the components in any desired sequence at temperature from 10 to 100° C., preferably 20 to 80° C. The components here also include the customary auxiliaries, which can be added to regulate the Theological properties, such as viscosity or water retention capacity, of the coating compositions. Such auxiliaries are, for example, natural binders, such as starch, casein, protein or gelatin, cellulose ethers, such as carboxyalkylcellulose or hydroxyalkylcellulose, alginic acid, alginates, polyethylene oxide or polyethylene oxide alkyl ethers, copolymers of ethylene oxide and propylene oxide, polyvinyl alcohol, water-soluble condensation products of formaldehyde with urea or melamine, polyphosphates or polyacrylic acid salts.

The coating composition used according to the method of the present invention is preferably used to produce coated printed or writing paper, or special papers such as ink-jet or photographic papers, or cardboard.

The coating composition used according to the method of the invention can be applied to the substrate by any conventional process, for example with an air blade, a coating blade, a roller, a doctor blade or a rod, or in the size press, after which the coatings are dried at paper surface temperatures in the range from 70 to 200° C., preferably 90 to 130° C., to a residual moisture content of 3-8%, for example with infra-red driers and/or hot-air driers. Comparably high degrees of whiteness are thus achieved even at low drying temperatures.

By the use of the method according to the Invention, the coatings obtained are distinguished by optimum distribution of the dispersion fluorescent brightener over the entire surface and by an increase in the level of whiteness thereby achieved, by a high fastness to light and to elevated temperature (e.g. stability for 24 hours at 60-100° C.) and excellent bleed-fastness to water.

In a second preferred aspect, the present invention provides a method for the fluorescent whitening of a paper surface comprising contacting the paper in the size press with an aqueous solution containing a size, optionally an inorganic or organic pigment and 0.1 to 20 g/l of a fluorescent whitening agent comprising a mixture of the compounds of formulae (1a), (1b) and (1c) according to the present invention. Preferably, the size is starch, a starch derivative or a synthetic sizing agent, especially a water-soluble copolymer.

In one further aspect of the invention, the mixture of the compounds of formulae (1a), (1b) and (1c) provide a method for increasing the SPF (Sun Protection Factor) rating or for the fluorescent whitening of a textile fibre material, comprising treating the textile fibre material with 0.05 to 5.0% by weight, based on the weight of the textile fibre material, with one or more mixtures of the compounds of formulae (1a), (1b) and (1c) of the invention, as previously defined.

Textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m$^2$ and have not been previously dyed in deep shades.

Some of the mixture of the compounds of formulae (1a), (1b) and (1c) used in the method of the present invention may be only sparingly soluble in water and may need to be applied in dispersed form. For this purpose, they may be milled with an appropriate dispersant, conveniently using quartz balls and an impeller, down to a particle size of 1-2 microns.

As dispersing agents for such sparingly-soluble mixture of the compounds of formulae (1a), (1b) and (1c) there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$-$C_6$alkanols, the addition products having been converted into an acid ester with an organic dicarboxylic acid or with an inorganic polybasic acid;

lignin sulphonates and, in particular, formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthylaminesulphonic acids and formaldehyde; condensation products of phenolsulphonic acids and/or sulphonated dihydroxydiphenylsulphone and phenols and cresols with formaldehyde and/or urea; or condensation products of diphenyloxide-disulphonic acid derivatives with formaldehyde.

Depending on the type of mixture of the compounds of formulae (1a), (1b) and (1c), it may be beneficial to carry out the treatment in a neutral, alkaline or acidic bath. The method is usually conducted in the temperature range of from 20 to 140° C., for example, at or near the boiling point of the aqueous bath, e.g., at about 90° C.

Solutions of the mixture of the compounds of formulae (1a), (1b) and (1c) or their emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the mixture of the compounds of formulae (1a), (1b) and (1c) in a concentration such that the desired SPF improvement or degree of whiteness is achieved.

In certain cases, the mixture of the compounds of formulae (1a), (1b) and (1c) is made fully effective by an after-treatment. This may comprise a chemical treatment such as treatment with an acid, a thermal treatment or a combined thermal/chemical treatment.

It is often advantageous to use the mixture of the compounds of formulae (1a), (1b) and (1c) in admixture with an assistant or extender such as sodium sulphate, sodium sulphate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the mixture of the compounds of formulae (1a), (1b) and (1c), a minor proportion of one or more adjuvants may also be employed in the method of the present invention. Examples of adjuvants include emulsifiers, perfumes, bleaching agents, enzymes, colouring dyes, opacifiers, further optical whitening agents, bactericides, nonionic surfactants, fabric care ingredients, anti-gelling agents such as nitrites or nitrates, especially sodium nitrate, and corrosion inhibitors such as sodium silicate.

The amount of each of these optional adjuvants should not exceed 1%, and preferably ranges from 0.01 to 1% by weight on the treated fibre.

The method of the present invention, in addition to providing protection to the skin, also increases the useful life of a textile article treated according to the present invention. In particular, the tear resistance and/or light fastness of the treated textile fibre material may be improved.

The present invention also provides a textile fabric produced from a fibre treated according to a method of the present invention as well as an article of clothing produced from the said fabric.

Such textile fabrics and articles of clothing produced from the said fabrics typically have an SPF rating of 20 and above, whereas untreated cotton, for example, generally has an SPF rating of from 2 to 4.

The fluorescent whitening agents of the present invention are particularly advantageous in that they exhibit not only extremely high whitening ability, excellent substantivity and fastness properties, but, in addition, in many cases highly desirable water solubilities, thus enabling ready preparation of stable concentrated liquid formulations.

The following Examples serve to illustrate the invention without intending to be restrictive in nature; parts and percentages are by weight, unless otherwise stated.

PREPARATIVE EXAMPLES

Example 1

A solution of 120 g of cyanuric chloride dissolved in 753 g of methyl ethyl ketone is poured onto 400 g of ice/water and the resulting suspension treated with 1041 g of an 11% aqueous solution of 4,4'-diaminostilbene-2,2'-disulphonic acid disodium salt over 70 minutes. During the addition the temperature rises to 10° C. and the pH is maintained at 4.0 by addition of a total of 64 ml of 20% aqueous sodium carbonate solution.

To the resulting suspension 56.6 g of morpholine are then slowly added at 15° C. and the reaction mixture then heated to 72° C. over 60 minutes. Stirring is then continued for a further 30 minutes, the pH being maintained at 7.0-7.5 by addition of 51 ml of aqueous 50% sodium hydroxide solution. After distilling off the methyl ethyl ketone, the reaction mixture is cooled to 25° C. and the precipitated solids filtered and dried. There are obtained 251 g of 4,4'-bis[(4-morpholino-6-chloro-1,3,5-triazin-2-yl)amino]stilbene-2,2'-disulphonic acid disodium salt with an active content of 88.2%.

9.2 g of the 4,4'-bis[(4-morpholino-6-chloro-1,3,5-triazin-2-yl)amino]stilbene-2,2'-disulphonic add disodium salt obtained as described above are suspended in 20 ml of water. To the resulting suspension, 1.26 g of diethanolamine, 1.60 g of aspartic acid and 2.93 g of 30% aqueous sodium hydroxide solution are added. The mixture is then heated to 94° C. and stirred for 5 hours at this temperature, the pH being maintained at 8.0-8.5 by addition of a total of 3.0 g of 30% aqueous sodium hydroxide solution. The mixture is then cooled, the water evaporated and the residue dried under vacuum to yield 14.0 g of a the fluorescent whitening agent (101), which comprises a mixture containing 25% of the compound (101a), 47% of compound (101b) and 22% compound (101c), according to HPLC analysis, in addition to 4.7% water.

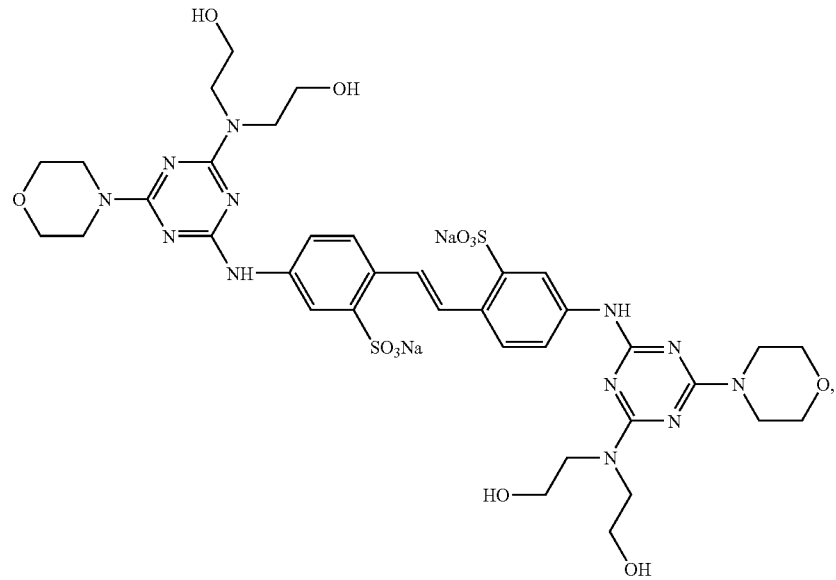

(101b)
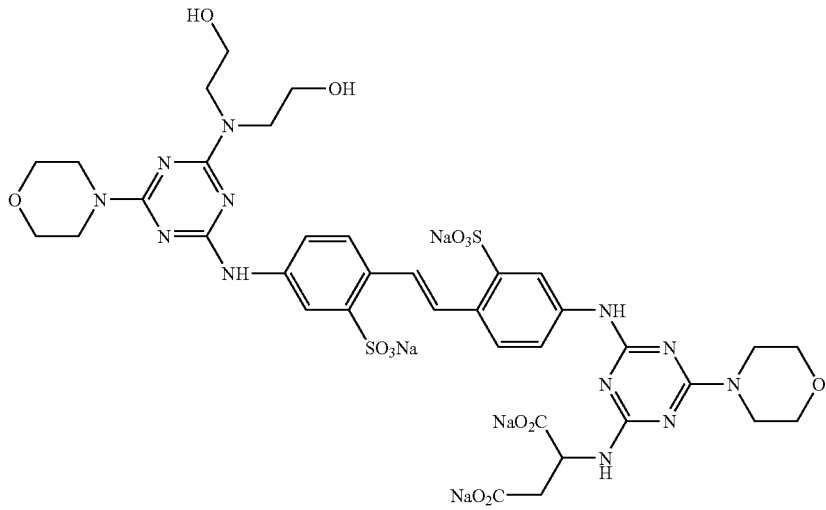
(101c)
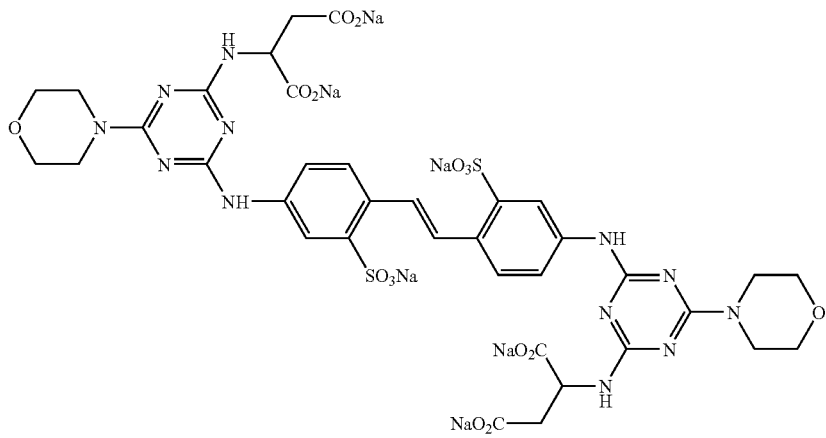
Examples 2-9
By proceeding as described in Example 1, but employing equivalent quantities of the appropriate amines $R_1H$ and $R_2H$ in the final reaction step, the following mixtures of fluorescent whitening agents of formulae (2a)-(2c) are obtained, as summarized in Table 1 below:
(2a)
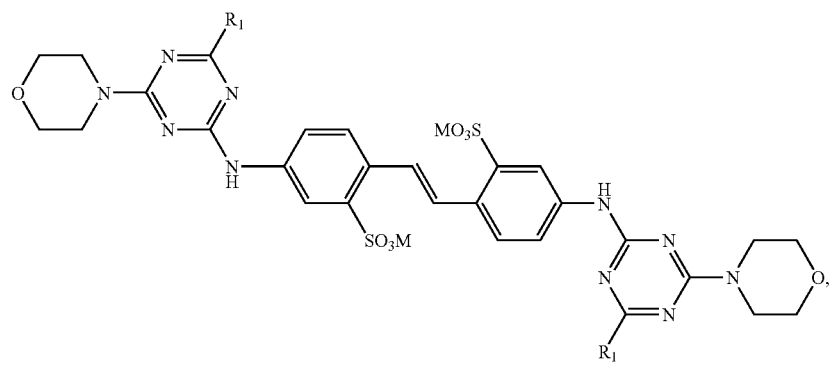

-continued

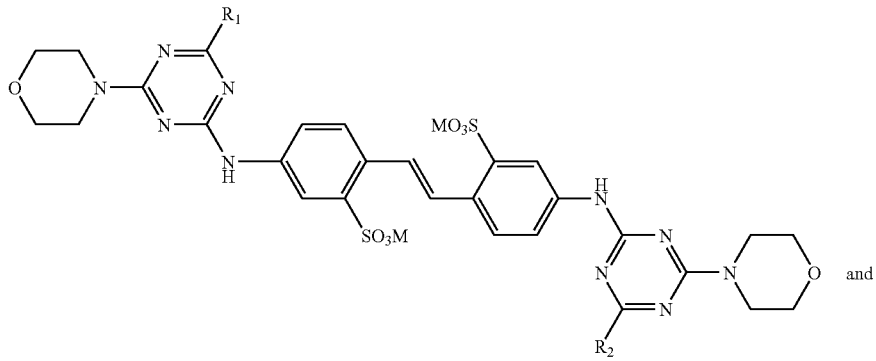

(2b)

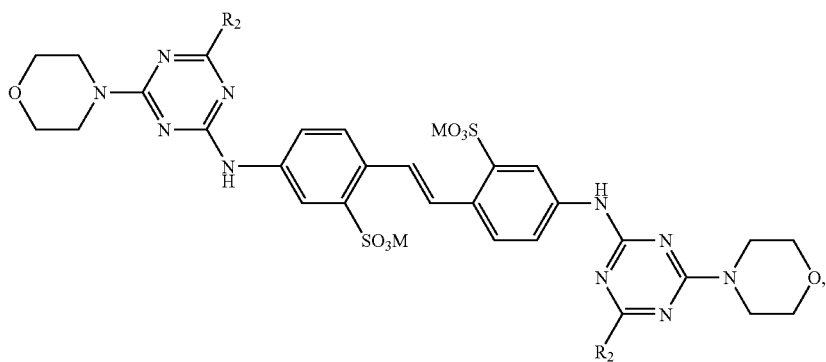

(2c)

whereby M represents sodium in all cases.

TABLE 1

| Example Nr. | $R_1$ | $R_2$ | Compound (2a) and % | Compound (2b) and % | Compound (2c) and % |
|---|---|---|---|---|---|
| 2 | —NHCH$_2$CH$_2$OH | —NHCH$_2$CO$_2$Na | (102a): 25% | (102b): 49% | (102c): 22% |
| 3 | —N(CH$_2$CHOH)$_2$ CH$_3$ | —NHCH$_2$CO$_2$Na | (103a): 20% | (103b): 48% | (102c): 30 |
| 4 | —N(CH$_2$CH$_2$OH)$_2$ | —NHCH$_2$CO$_2$Na | (101a)[1] | (104b)[1] | (102c)[1] |
| 5 | —N(CH$_2$CH$_3$)$_2$ | —NHCH$_2$CO$_2$Na | (105a): 16% | (105b): 36% | (102c): 37% |
| 6 | —NCH$_2$CH$_2$OH CH$_3$ | —NHCH$_2$CO$_2$Na | (106a): 35% | (106b): 40% | (102c): 23% |
| 7 | —NHCH$_2$CH$_2$OH | —NHCHCO$_2$Na CO$_2$Na | (102a): 21% | (107b): 38% | (101c): 35% |
| 8 | —N(CH$_2$CH$_3$)$_2$ | —NHCHCO$_2$Na CO$_2$Na | (105a): 24% | (108b): 38% | (101c): 30% |
| 9 | —NCH$_2$CH$_2$OH CH$_3$ | —NHCHCO$_2$Na CO$_2$Na | (106a)[2] | (109b)[2] | (101c)[2] |
| 10 | —NCH$_2$CO$_2$H CH$_3$ | —NHCHCO$_2$Na CO$_2$Na | (110a): 26% | (110b): 41% | (101c): 26% |

TABLE 1-continued

| Example Nr. | R$_1$ | R$_2$ | Compound (2a) and % | Compound (2b) and % | Compound (2c) and % |
|---|---|---|---|---|---|
| 11 | —NCH$_2$CH$_2$OH<br>H$_2$C<sub>\</sub>C<sub>/</sub>CONH$_2$<br>H$_2$ | —NHCH$_2$CO$_2$Na | (111a): 16% | (111b): 45% | (102c): 32% |
| 12 | —N(morpholino) | —NHCHCO$_2$Na<br>\|<br>CO$_2$Na | (112a): 28% | (112b): 37% | (101c): 28% |
| 13 | —N(morpholino) | —NHCH$_2$CO$_2$Na | (112a): 28% | (113b): 42% | (113c): 28% |

Footnotes:
[1] The sum of the components (104a)-(104c) amounts to 94% of the isolated material by HPLC, but individual ratios were not established.
[2] The sum of the components (109a)-(109c) amounts to 95% of the isolated material by HPLC, but individual ratios were not established.

Application Examples 14-33

To a coating colour having a solids content of 70% and consisting of 70% calcium carbonate and 30% clay, 0.2 parts of polyvinyl alcohol and 9 parts of SBR binder, based on the weight of the pigment, are added followed by varying amounts of the fluorescent whitening agents of the above Examples. After stirring for 15 minutes to homogenize the coating colour, an 85 g/m$^2$ neutral sized base paper free of fluorescent whitening agent is coated using a laboratory blade coater with a coating speed of 6 m/min. such that a coat weight of 13 18±0.5 g/m$^2$ results. After drying, the CIE Whiteness and ISO-fluorescence values are measured using a Datacolor Elrepho 3000 spectrophotometer.

The results are summarized in the following Table 2:

TABLE 2

| Example Nr. | % FWA/Example Nr. | W(CIE) | F(ISO) |
|---|---|---|---|
|  | None | 74.3 | 0.0 |
| 14 | 0.2/Eg. 2 | 92.6 | 5.3 |
| 15 | 0.4/Eg. 2 | 96.6 | 6.8 |
| 16 | 0.2/Eg. 3 | 93.4 | 5.5 |
| 17 | 0.4/Eg. 3 | 97.4 | 7.0 |
| 18 | 0.2/Eg. 4 | 93.1 | 5.6 |
| 19 | 0.4/Eg. 4 | 96.3 | 6.8 |
| 20 | 0.2/Eg. 6 | 93.3 | 5.6 |
| 21 | 0.4/Eg. 6 | 97.1 | 6.9 |
| 22 | 0.2/Eg. 7 | 93.3 | 5.6 |
| 23 | 0.4/Eg. 7 | 95.4 | 6.4 |
| 24 | 0.2/Eg. 8 | 92.7 | 5.4 |
| 25 | 0.4/Eg. 8 | 96.5 | 6.8 |
| 26 | 0.2/Eg. 10 | 93.5 | 5.7 |
| 27 | 0.4/Eg. 10 | 96.3 | 6.8 |
| 28 | 0.2/Eg. 11 | 92.4 | 5.3 |
| 29 | 0.4/Eg. 11 | 94.1 | 6.7 |
| 30 | 0.2/Eg. 12 | 92.8 | 5.5 |
| 31 | 0.4/Eg. 12 | 96.2 | 6.7 |
| 32 | 0.2/Eg. 13 | 93.0 | 5.5 |
| 33 | 0.4/Eg. 13 | 97.0 | 6.9 |

The above results clearly indicate the excellent whitening effects achieved by the fluorescent whitening agents of the invention when used for paper coatings.

The invention claimed is:

1. A fluorescent whitening agent, which comprises a mixture of compounds of the formulae

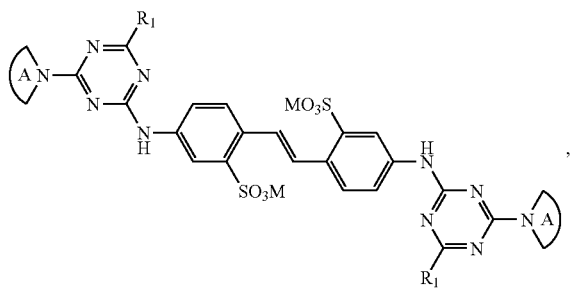

(1a)

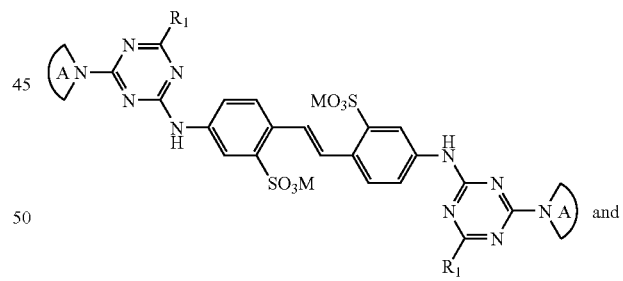

(1b)

and

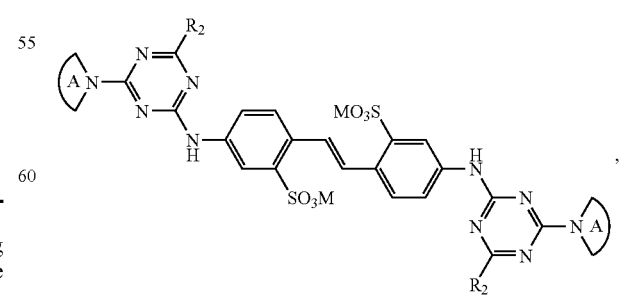

(1c)

in which $R_1$ and $R_2$ are different and are not derived from the same amino acid or amino acid amide residue $R_1$ is —$NH_2$, —$NHC_1$-$C_4$alkyl, —$N(C_1$-$C_4$alkyl$)_2$, —$NHC_2$-$C_4$hydroxyalkyl, —$N(C_2$-$C_4$hydroxyalkyl$)_2$, —$N(C_1$-$C_4$alkyl)($C_2$-$C_4$ hydroxyalkyl), a morpholino residue or an amino acid or an amino acid amide residue from which a hydrogen atom has been removed from the amino group, $R_2$ is an amino acid or an amino acid amide residue from which a hydrogen atom has been removed from the amino group, each of the rings designated as A represent a 5- or 6-membered saturated heterocycle, which may contain one further heteroatom and M represents hydrogen, an alkali metal atom, ammonium or a cation formed from an amine.

2. A fluorescent whitening agent, according to claim 1, which comprises a mixture of compounds of the formulae 3. A fluoresent whitening agent according to claim 1, in which the aliphatic amino acid or amino acid amide residue is of the formula $$—NR_3—CH(CO_2H)—R_{3'} \qquad (3)$$

or $$—NR_3—CH_2CH_2CONH_2 \qquad (4),$$

in which each $R_3$ and $R_{3'}$, independently, represent hydrogen or a group having the formula —$CHR_4R_5$ in which $R_4$ and $R_5$, independently, are hydrogen or $C_1$-$C_4$alkyl optionally substituted by one or two substituents selected from the group consisting of hydroxy, thio, methylthio, amino, carboxy, sulfo, phenyl, 4-hydrox-

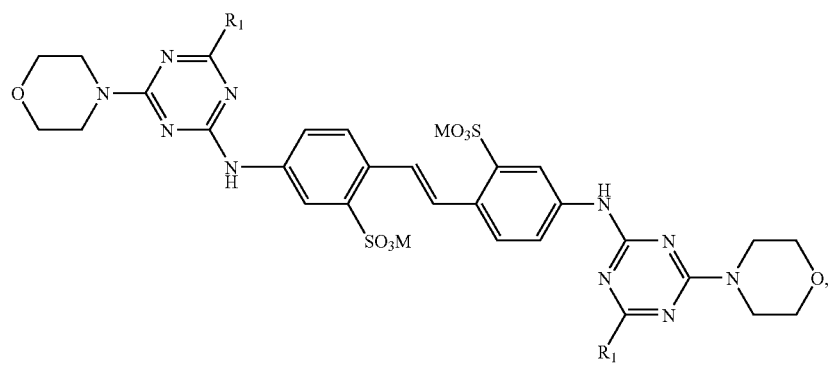

(2a)

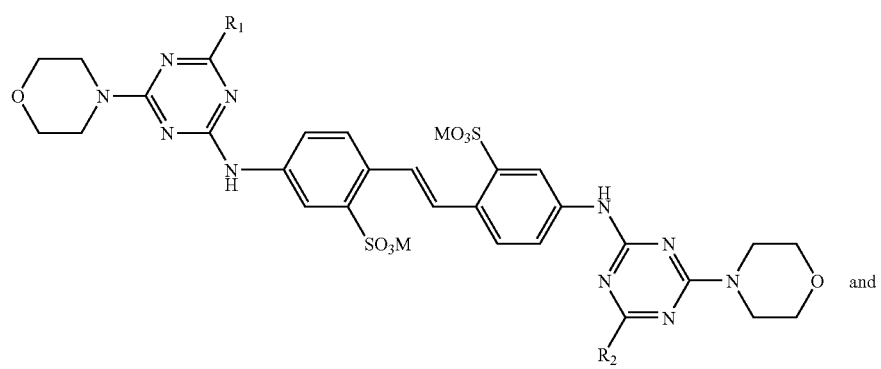

(2b)

and

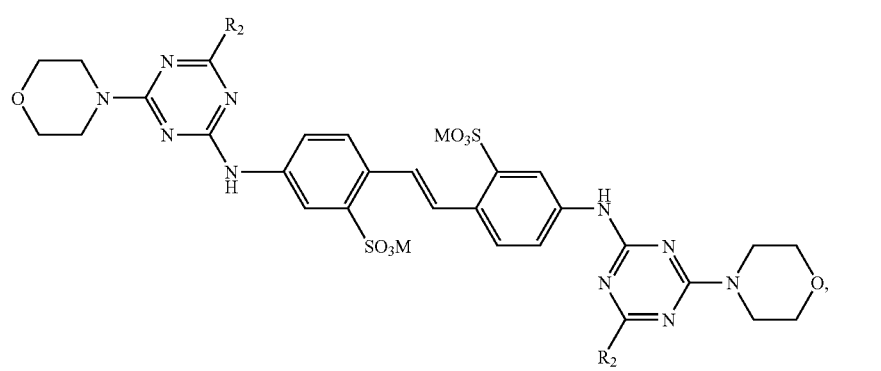

(2c)

in which $R_1$, $R_2$ and M are as defined in claim 1.

yphenyl, 3,5-diiodo-4-hydroxyphenyl, β-indolyl, β-imidazolyl and NH=C(NH$_2$)NH—.

4. A fluorescent whitening agent according to claim 3, in which residues $R_1$ and $R_2$ are derived from glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid, iminodiacetic acid, N-(propionamido)-N-(2-hydroxethyl)amine, taurine, and mixtures and optical isomers thereof.

5. A fluorescent whitening agent according to claim 1, in which $R_1$ is —N(C$_1$-C$_4$alkyl)$_2$, —NHC$_2$-C$_4$hydroxyalkyl, —N(C$_2$-C$_4$ hydroxyalkyl)$_2$, —N(C$_1$-C$_4$alkyl)(C$_2$-C$_4$hydroxyalkyl), a morpholino residue a residue derived from glycine, sarcosine, taurine, glutamic acid, aspartic acid, iminodiacetic acid or from N-(propionamido)-N-(2-hydroxyethyl)amine.

6. A fluorescent whitening agent according to claim 5 in which $R_1$ represents a mono-(2-hydroxyethyl)amino, a di-(2-hydroxyethyl) amino, a di-(2-hydroxypropyl)amino, a diethylamino, an N-(2-hydroxyethyl)-N-methylamino, a morpholino, an N-(propionamido)-N-(2-hydroxyethyl)amino or a sarcosine residue and $R_2$ represents an aspartic acid or a glycine residue.

7. A fluorescent whitening agent according to claim 1, in which

M represents hydrogen, lithium, potassium, sodium, ammonium, mono-, di-, tri- or tetra-C$_1$-C$_4$alkylammonium, mono-, di- or tri-C$_1$-C$_4$hydroxyalkylammonium or ammonium that is di- or tri-substituted with a mixture of C$_1$-C$_4$alkyl and C$_1$-C$_4$hydroxyalkyl groups.

8. A fluorescent whitening agent according to claim 7, in which

M represents hydrogen, potassium or sodium.

9. A process for the preparing the fluorescent whitening agent mixture of compounds of formulae (1a), (1b) and (1c) according to claim 1 by reacting, under known reaction conditions, cyanuric chloride with each of 4,4'-diaminostilbene-2,2'-disulphonic acid, an appropriate heterocyclic compound, an amino compound $R_1$H and an amino compound $R_2$H, or, alternatively a mixture of amino compounds $R_1$H and $R_2$H, $R_1$ and $R_2$ are as defined in claim 1.

10. A compound of the formula

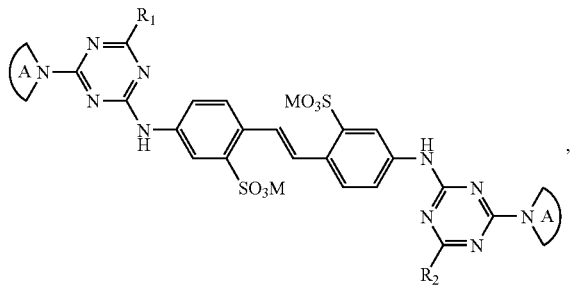

(1b)

in which $R_1$ and $R_2$ are different and are not derived from the same amino acid or amino acid amide residue $R_1$ is —NH$_2$, —NHC$_1$-C$_4$alkyl, —N(C$_1$-C$_4$alkyl)$_2$, —NHC C$_2$-C$_4$ hydroxyalkyl, —N(C$_2$-C$_4$hydroxyalkyl)$_2$, —N(C$_1$-C$_4$alkyl)(C$_2$-C$_4$ hydroxyalkyl), a morpholino residue or an amino acid or an amino acid amide residue from which a hydrogen atom has been removed from the amino group, $R_2$ is an amino acid or an amino acid amide residue from which a hydrogen atom has been removed from the amino group, each of the rings designated as A represent a 5- or 6-membered saturated heterocycle, which may contain one further heteroatom and M reeresents hydrogen, an alkali metal atom, ammenium or a cation formed from an amine.

11. A compound of formula

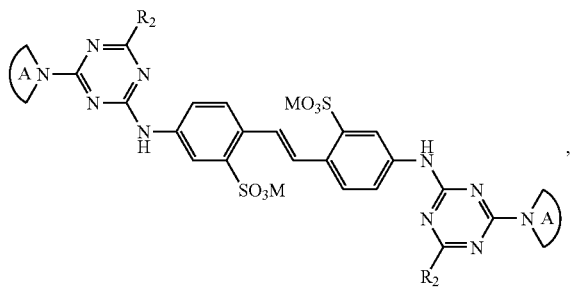

(1c)

in which $R_2$ is an amino acid or amino acid derivative from which a hydrogen atom has been removed from the amino group, whereby the residue is derived from alanine, sarcosine, serine, cysteine, phenylalanine, tyrosine (4-hydroxyphenylalanine), diiodotyrosine, tryptophan (β-indolylalanine), histidine (β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine iminodiacetic acid, N-(propionamido)-N-(2-hydroxethyl)amine or corresponding propionic acid, hydroxyglutamic acid, and mixtures and optical isomers thereof, each of the rings designated as A represent a 5- or 6-membered saturated heterocycle, which may contain one further heteroatom and M represents hydrogen, an alkali metal atom, ammonium or a cation formed from an amine.

12. A method for whitening synthetic or natural organic material by treating the synthetic or natural material with a composition, which contains water, a fluorescent whitening agent, which comprises a mixture of the compounds (1a), (1b) and (1c), a compound of formula (1b) or a compound of formula (1c)

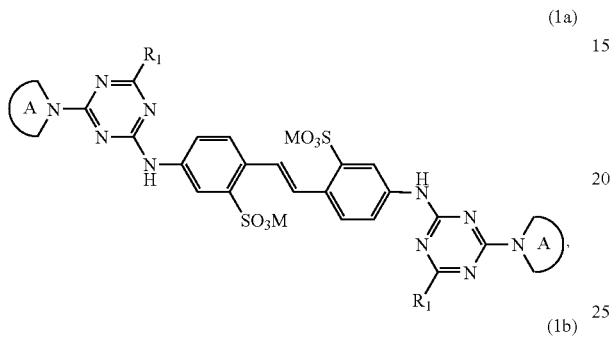

or a compound of formula (1c)

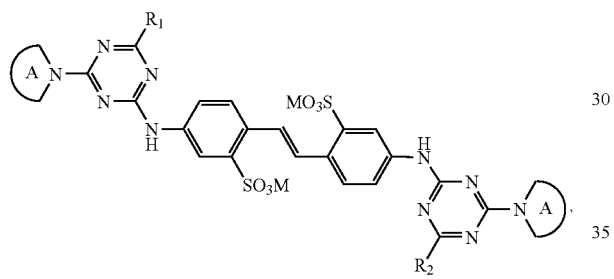

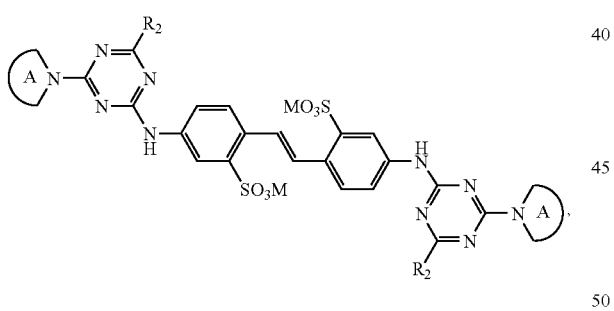

in which
R$_1$ and R$_2$ are different and are not derived from the same amino acid or amino acid amide residue
R$_1$ is —NH$_2$, —NHC$_1$-C$_4$alkyl, —N(C$_1$-C$_4$alkyl)$_2$, —NHC$_2$-C$_4$ hydroxyalkyl, —N(C$_2$-C$_4$hydroxyalkyl)$_2$, —N(C$_1$-C$_4$alkyl)(C$_2$-C$_4$ hydroxyalkyl), a morpholino residue or an amino acid or an amino acid amide residue from which a hydrogen atom has been removed from the amino group,
R$_2$ is an amino acid or amino acid derivative from which a hydrogen atom has been removed from the amino group, whereby the residue is derived from alanine, sarcosine, serine, cysteine, phenylalanine, tyrosine (4-hydroxyphenylalanine), diiodotyrosine, tryptophan (β-indolylalanine), histidine (β-imidazolylalanine), α-aminobutyric acid, methionine, valine (α-aminoisovaleric acid), norvaline, leucine (α-aminoisocaproic acid), isoleucine α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid α-aminoglutaric acid), threonine or hydroxyglutamic acid, as well as mixtures and optical isomers thereof, or from iminodiacetic acid or from N-(propionamido)-N-(2-hydroxyethyl)amine or the corresponding propionic acid, each of the rings designated as A represent a 5- or 6-membered saturated heterocycle, which may contain one further heteroatom and M represents hydrogen, an alkali metal atom, ammonium or a cation formed from an amine and, optionally, auxiliaries.

13. A method according to claim 12 for whitening of paper comprising applying to the paper substrate in the pulp mass, in the form of a paper coating composition, or directly in the size press or metering press a mixture of compounds (1a), (1b) and (1c), a compound (1b) or a compound (1c).

14. Paper, which has been optically brightened by the compound mixture of formulae (1a), (1b) and (1c), a compound of formula (1b) or a compound of formula(1c)

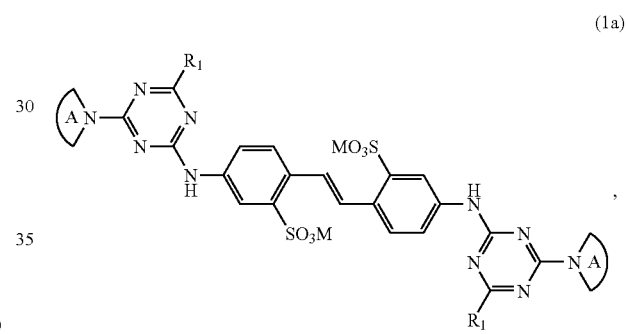

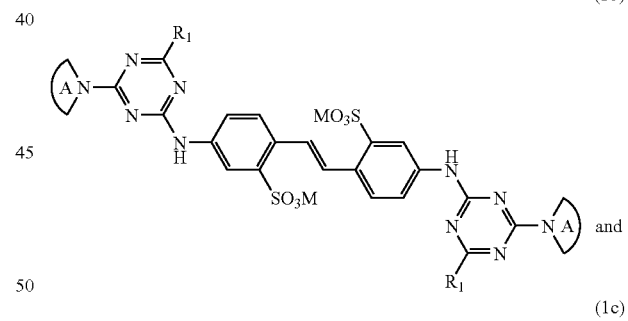

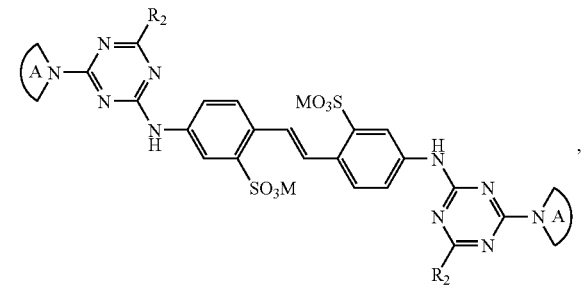

in which
R$_1$ and R$_2$ are different and are not derived from the same amino acid or amino acid amide residue $R_1$ is —$NH_2$, —$NHC_1$-$C_4$alkyl, —$N(C_1$-$C_4$alkyl$)_2$, —$NHC_2$-$C_4$ hydroxyalkyl, —$N(C_2$-$C_4$hydroxyalkyl$)_2$, —$N(C_1$-$C_4$alkyl)($C_2$-$C_4$ hydroxyalkyl), a morpholino residue or an amino acid or an amino acid amide residue from which a hydrogen atom has been removed from the amino group, $R_2$ is an amino acid or amino acid derivative from which a hydrogen atom has been removed from the amino group, whereby the residue is derived from alanine, sarcosine, serine, cysteine, phenylalanine, tyrosine (4-hydroxyphenylalanine), diiodotyrosine, tryptophan (β-indolylalanine), histidine (β-imidazolylalanine), α-aminobutyric acid, methionine, valine (α-aminoisovaleric acid), norvaline, leucine (α-aminoisocaproic acid), isoleucine α-amino-β-methylvaleric acid), norleucine α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine or hydroxyglutamic acid, as well as mixtures and optical isomers thereof, or from iminodiacetic acid or from N-(Propionamido)-N-(2-hydroxyethyl)amine or the corresponding propionic acid, each of the rings designated as A represent a 5- or 6-membered saturated heterocycle, which may contain one further heteroatom and M represents hydrogen, an alkali metal atom. ammonium or a cation formed from an amine.

15. A method according to claim 12, for increasing the Sun Protection Factor (SPF) rating or for the fluorescent whitening of a textile fibre materials.

16. A textile fabric produced from a fibre treated with the compound mixture of formulae (1a), (1b) and (1c), a compound of formula (1b) or a compound of formula (1c)

(1a)

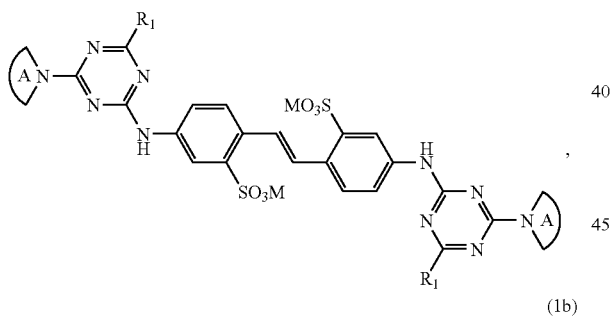

(1b)

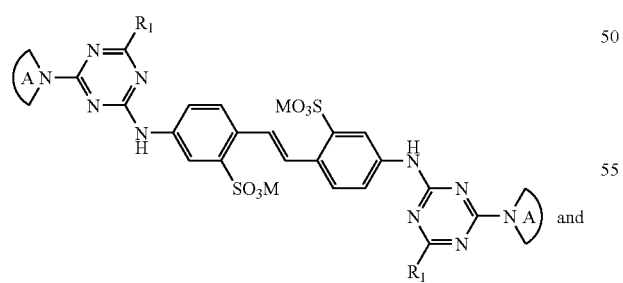

and

-continued (1c)

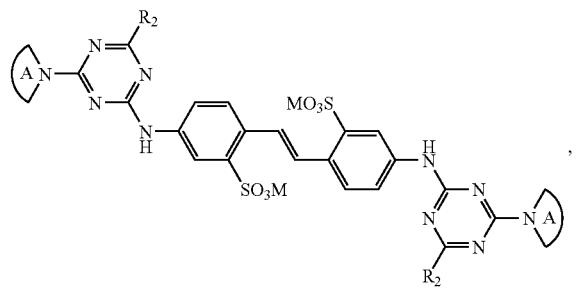

in which $R_1$ and $R_2$ are different and are not derived from the same amino acid or amino acid amide residue $R_1$ is —$NH_2$, —$NHC_1$-$C_4$alkyl, —$N(C_1$-$C_4$alkyl$)_2$, —$NHC_2$-$C_4$ hydroxyalkyl, —$N(C_2$-$C_4$hydroxyalkyl$)_2$, —$N(C_1$-$C_4$alkyl)($C_2$-$C_4$ hydroxyalkyl), a morpholino residue or an amino acid or an amino acid amide residue from which a hydrogen atom has been removed from the amino group, $R_2$ is an amino acid or amino acid derivative from which a hydrogen atom has been removed from the amino group, whereby the residue is derived from alanine, sarcosine, serine, cysteine, phenylalanine, tyrosine (4-hydroxyphenylalanine), diiodotyrosine, tryptophan (β-indolylalanine), histidine (β-imidazolylalanine), α-aminobutyric acid, methionine, valine (α-aminoisovaleric acid), norvaline, leucine α-aminoisocaproic acid), isoleucine α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, iminodiacetic acid, N-(propionamido)-N-(2-hydroxyethyl)amine or the corresponding proionic acid hydroxyglutamic acid, and mixtures and optical isomers thereof, each of the rings designated as A represent a 5- or 6-membered saturated heterocycle, which may contain one further heteroatom and M represents hydrogen, an alkali metal atom, ammonium or a cation formed from an amine.

* * * * *

UNITED STATES PATENT AND TRADEMARK OFFICE
CERTIFICATE OF CORRECTION

PATENT NO. : 7,585,333 B2 Page 1 of 1
APPLICATION NO. : 10/585956
DATED : September 8, 2009
INVENTOR(S) : Cuesta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this

Fourteenth Day of September, 2010

David J. Kappos
*Director of the United States Patent and Trademark Office*